(12) United States Patent
Kunisada

(10) Patent No.: US 9,827,069 B2
(45) Date of Patent: Nov. 28, 2017

(54) DENTAL HANDPIECE CONTROL APPARATUS

(71) Applicant: NAKANISHI INC., Tochigi (JP)

(72) Inventor: Makoto Kunisada, Tochigi (JP)

(73) Assignee: NAKANISHI INC., Tochigi (JP)

( * ) Notice: Subject to any disclaimer, the term of this patent is extended or adjusted under 35 U.S.C. 154(b) by 0 days.

(21) Appl. No.: 14/361,583

(22) PCT Filed: Jan. 11, 2013

(86) PCT No.: PCT/JP2013/000091
§ 371 (c)(1),
(2) Date: May 29, 2014

(87) PCT Pub. No.: WO2013/108602
PCT Pub. Date: Jul. 25, 2013

(65) Prior Publication Data
US 2014/0322669 A1    Oct. 30, 2014

(30) Foreign Application Priority Data

Jan. 16, 2012  (JP) .................................. 2012-005798

(51) Int. Cl.
*A61C 5/02* (2006.01)
*A61C 1/00* (2006.01)
(Continued)

(52) U.S. Cl.
CPC .............. *A61C 5/023* (2013.01); *A61C 1/003* (2013.01); *A61C 1/186* (2013.01); *A61C 5/40* (2017.02);
(Continued)

(58) Field of Classification Search
CPC ........... A61C 5/02; A61C 5/023; A61C 1/003; A61C 1/186; A61C 19/042
(Continued)

(56) References Cited

U.S. PATENT DOCUMENTS 5,383,105 A    1/1995  Agut
5,980,248 A *  11/1999  Kusakabe ............ A61C 1/0007
                                                433/131
(Continued)

FOREIGN PATENT DOCUMENTS

EP    2 716 254 A1    4/2014
JP    57-180951 A     11/1982
(Continued)

OTHER PUBLICATIONS

International Search Report for Application No. PCT/JP2013/000091 dated Apr. 16, 2013.
(Continued)

*Primary Examiner* — Matthew Nelson
(74) *Attorney, Agent, or Firm* — Pearne & Gordon LLP

(57) ABSTRACT

A dental handpiece control apparatus including: a relay 17 that switches a polarity of a voltage applied to a motor 20, and thereby switches a rotation direction of the motor 20 to forward rotation and backward rotation, the motor 20 being incorporated in the dental handpiece to rotate a cutting tool (a file) mounted to the dental handpiece; and a control section 11 that controls the switching of the voltage polarity by the relay 17 based on a rotation angle $\theta_F$ for forward rotation and a rotation angle $\theta_R$ for backward rotation of the motor 20, the rotation angle $\theta_F$ and the rotation angle $\theta_R$ being associated with state information of the file.

7 Claims, 8 Drawing Sheets

(51) Int. Cl.
*A61C 1/18* (2006.01)
*A61C 19/04* (2006.01)
*A61C 5/40* (2017.01)

(52) U.S. Cl.
CPC .... *A61C 19/042* (2013.01); *F04C 2270/0421* (2013.01)

(58) Field of Classification Search
USPC ............ 433/27, 81, 102, 118, 122, 131, 224
See application file for complete search history.

(56) References Cited

U.S. PATENT DOCUMENTS

| | | | | |
|---|---|---|---|---|
| 6,293,795 | B1* | 9/2001 | Johnson | A61C 1/0015 433/102 |
| 2002/0064756 | A1* | 5/2002 | Pagnini | A61C 5/02 433/102 |
| 2005/0042572 | A1* | 2/2005 | Katsuda | A61C 1/0015 433/98 |
| 2012/0094252 | A1* | 4/2012 | Johnson | A61C 5/023 433/102 |
| 2012/0122055 | A1* | 5/2012 | Ramos | A61C 1/003 433/102 |
| 2012/0225406 | A1* | 9/2012 | Yared | 433/102 |

FOREIGN PATENT DOCUMENTS

| | | |
|---|---|---|
| JP | 62-11442 A | 1/1987 |
| JP | 2003-19143 A | 1/2003 |
| JP | 2003-504113 A | 2/2003 |
| WO | 01/03601 A1 | 1/2001 |
| WO | 2010/066337 A1 | 6/2010 |
| WO | 2011/067723 A2 | 6/2011 |
| WO | 2012/001869 A1 | 1/2012 |
| WO | 2012/164875 A1 | 12/2012 |

OTHER PUBLICATIONS

Extended European Search Report for Application No. 13738184.4 dated Aug. 26, 2015.

* cited by examiner

DENTAL HANDPIECE CONTROL APPARATUS

TECHNICAL FIELD

The present invention relates to an apparatus for controlling a dental handpiece to cut the root canals of teeth.

BACKGROUND ART

Dental handpieces to cut the root canals of teeth have a configuration in which a cutting tool called a file is rotated by a motor.

Here, the file that cuts the root canals of teeth has a thin long form. When the file bites into a tooth at the time of cutting the root canal of the tooth, a force in a twist direction is applied to the file, resulting in a problem that the file is easily broken.

Thus, there has been proposed a method for preventing biting of the file into the root canal of a tooth and breakage thereof by repeating forward and backward rotations in which the file is rotated in one direction for a given time, and thereafter rotated in an opposite direction (simply referred to as "forward and backward rotations" below) (e.g., see Patent Literature 1). Repeating the forward rotation and the backward rotation as described above is sometimes called reciprocating rotation. The forward rotation and the backward rotation do not indicate rotation in a particular direction, but a preceding rotation direction is referred to as forward rotation.

In the method of performing the forward and backward rotations according to Patent Literature 1, the file is rotated clockwise or counterclockwise through a desired first rotation angle, and subsequently rotated in a direction opposite to the first rotation angle through a second rotation angle. The first rotation angle is larger than the second rotation angle such that cut debris removed from the root canal is ejected upwardly from the surface of the root canal when the file is advanced in cleaning the root canal.

CITATION LIST

Patent Literature

Patent Literature 1: National Publication of International Patent Application, JP2003-504113A

SUMMARY OF INVENTION

Technical Problem

In accordance with the method of Patent Literature 1, however, the first rotation angle and the second rotation angle are fixed to preset values, e.g., 120° C. and 90° C., respectively. Therefore, even when a load is increased, the file continues to rotate up to the set angle, and the file sometimes bites into the root canal, thereby possibly causing breakage of the file.

The present invention has been accomplished in view of the technical problem as described above, and an object thereof is to provide a dental handpiece control apparatus which can prevent a file that performs reciprocating rotation from biting into a root canal.

Solution to Problem

Based on the object, a dental handpiece control apparatus according to the present invention includes: a rotation direction switching section that switches a polarity of a voltage applied to a motor, and thereby switches a rotation direction of the motor to forward rotation and backward rotation, the motor being incorporated in the dental handpiece to rotate a cutting tool (a file) mounted to the dental handpiece; and a control section that controls the switching of the voltage polarity by the rotation direction switching section based on a rotation angle $\theta_F$ for forward rotation and a rotation angle $\theta_R$ for backward rotation of the motor, the rotation angle $\theta_F$ and the rotation angle $\theta_R$ being associated with state information of the cutting tool.

In accordance with the control apparatus of the present invention, the rotation angle $\theta_F$ for forward rotation and the rotation angle $\theta_R$ for backward rotation are set to values with which the cutting tool in the state does not bite into a root canal, so that the cutting tool can be prevented from biting into the root canal.

In the present invention, the rotation angle $\theta_F$ for forward rotation means a rotation angle for forward rotation of one cycle, and the rotation angle $\theta_R$ for backward rotation means a rotation angle for backward rotation of one cycle.

In the control apparatus of the present invention, the state information of the cutting tool may be a load torque of the motor. In this case, the control section preferably controls the switching of the voltage polarity by the rotation direction switching section based on the rotation angle $\theta_F$ and the rotation angle $\theta_R$ associated with the load torque. This is because the load torque of the motor can most notably indicate the biting of the cutting tool among the state information of the cutting tool.

In the control apparatus of the present invention, the load torque of the motor and the rotation angle $\theta_F$, and the load torque of the motor and the rotation angle $\theta_R$ may be respectively in a proportional relationship.

Also, in the control apparatus of the present invention, the rotation angle $\theta_F$ and the rotation angle $\theta_R$ may be different from each other with a reference value of the load torque of the motor as a boundary.

Advantageous Effects of Invention

In accordance with the present invention, the dental handpiece control apparatus which can prevent the cutting tool (the file) that performs reciprocating rotation from biting into the root canal can be provided.

DESCRIPTION OF EMBODIMENTS

First Embodiment

In the following, the present invention is described in detail based on embodiments shown in the accompanying drawings.

Figure 1:
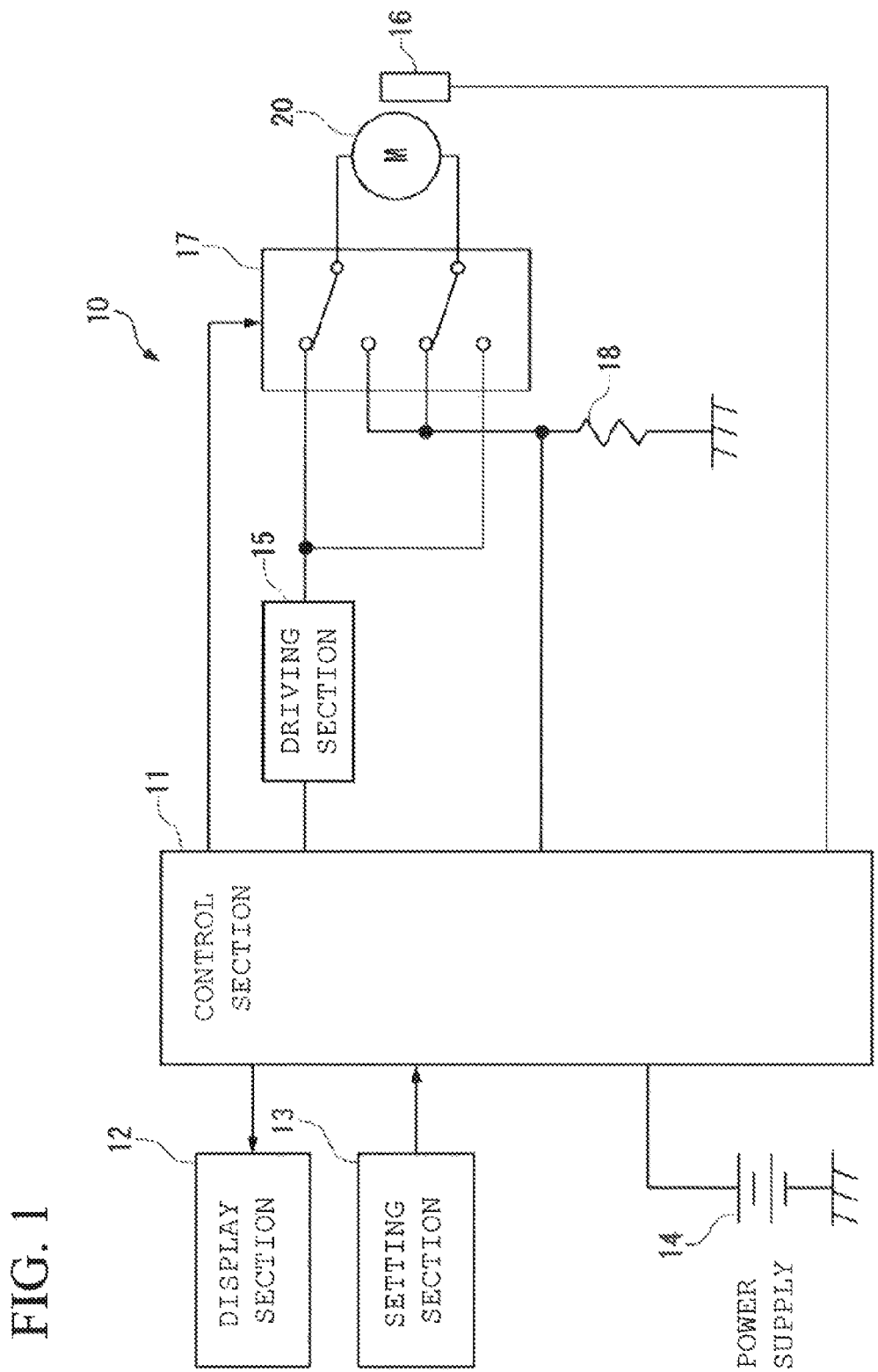
FIG. 1 is a view for explaining the configuration of a dental handpiece control apparatus in a present embodiment (a first embodiment).

As shown in FIG. 1, a control apparatus 10 for a dental handpiece (simply referred to as handpiece below) controls operation of a motor 20 that is incorporated in an unillustrated handpiece. The control apparatus 10 includes a control section 11, a display section 12, a setting section 13, a power supply 14, a driving section 15, a sensor 16, a relay (a rotation direction switching section) 17, and a current detecting resistor 18.

The control section 11 is a computer unit including a CPU, a memory or the like.

The display section 12 includes a monitor, an indicator lamp or the like for displaying information indicative of a rotation speed, a load torque as an operating state of the motor 20, or information used for setting the operation of the motor 20 or the like in the control section 11.

The setting section 13 sets operating conditions such as a rotation speed, a torque, and a rotation angle of the motor 20 for the control section 11, and retains the set information. Particularly, the setting section 13 in the present embodiment retains set information regarding a rotation angle $\theta_F$ for forwardly rotating the motor 20, and a rotation angle $\theta_R$ for backwardly rotating the motor 20.

The power supply 14 supplies electric power for allowing the handpiece control apparatus 10 and the motor 20 to work.

The driving section 15 adjusts a voltage value applied to the motor 20 based on a command from the control section 11.

The sensor 16 includes a hall element for detecting the rotation angle of the motor 20, and an encoder.

The relay 17 switches the voltage polarity applied to the motor 20.

The current detecting resistor 18 detects a current having passed through the relay 17, and converts a current (a motor current) having passed through the motor 20 to a voltage and feeds it back to the control section 11. Since a motor current and a load torque are in a proportional relationship in a DC motor, the control section 11 can measure the load toque of the motor 20 based on the fed-back voltage value.

Although any type of motor may be employed as the motor 20, for example, a brushless DC motor can be used.

Figure 2:
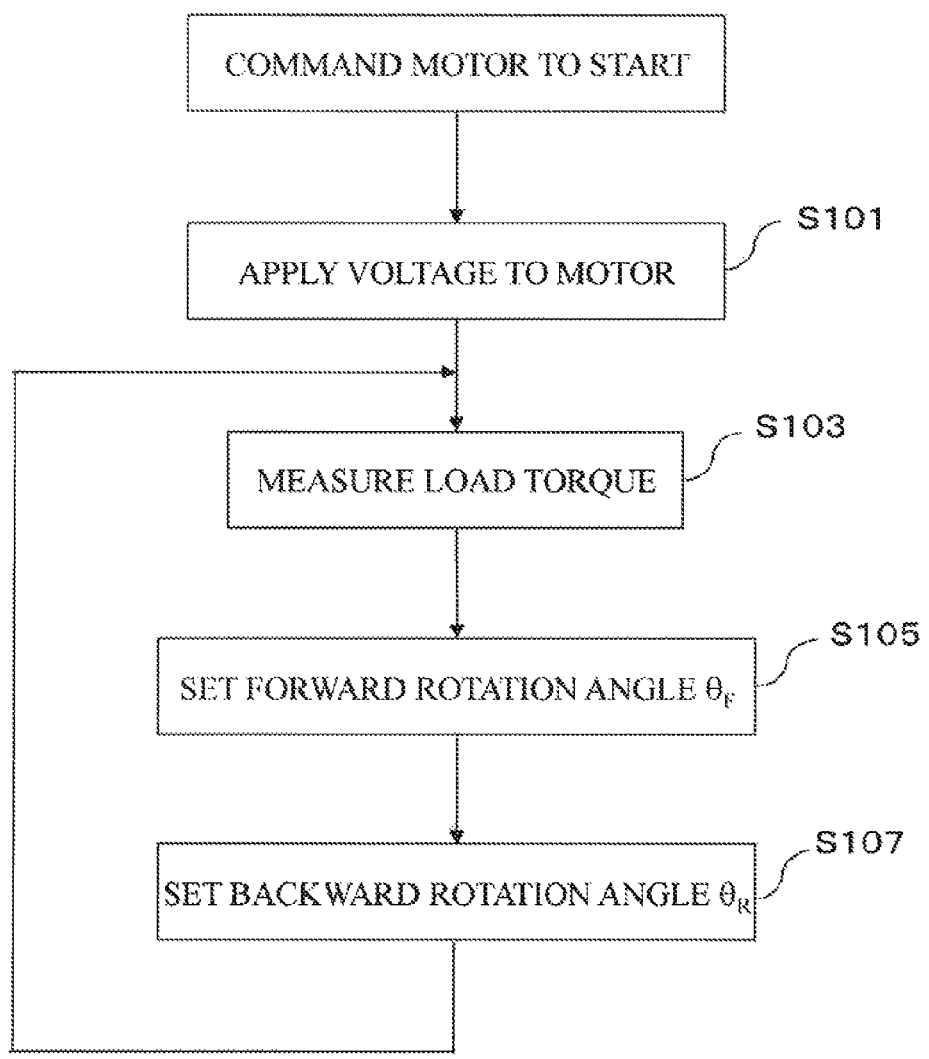
FIG. 2 is a view illustrating a control procedure in the control apparatus according to the first embodiment.

Next, the content of controlling the operation of the motor 20 in the handpiece control apparatus 10 as described above is described by using FIGS. 2 and 3.

When a switch or the like for operating the handpiece is manipulated, the control apparatus 10 executes control as described below based on a preset computer program.

First, voltage application to the motor 20 is started based on a command from the control section 11 (step S101). Here, the control section 11 detects the rotation speed of the motor by the sensor 16, and adjusts the voltage applied to the motor 20 such that the detected value matches a set value (a set speed) of the rotation speed of the motor 20 set in advance in the setting section 13.

The control section 11 also measures the load torque via the current detecting resistor 18 (step S103).

Based on the measured load torque, the control section 11 sets the rotation angle $\theta_F$ for forwardly rotating the motor 20, and the rotation angle $\theta_R$ for backwardly rotating the motor 20 according to the load torque (step S105, S107). The rotation angles are set by referring to the information preliminarily retained in the setting section 13 as described above. One example of the information is described based on FIG. 3.

Figure 3:
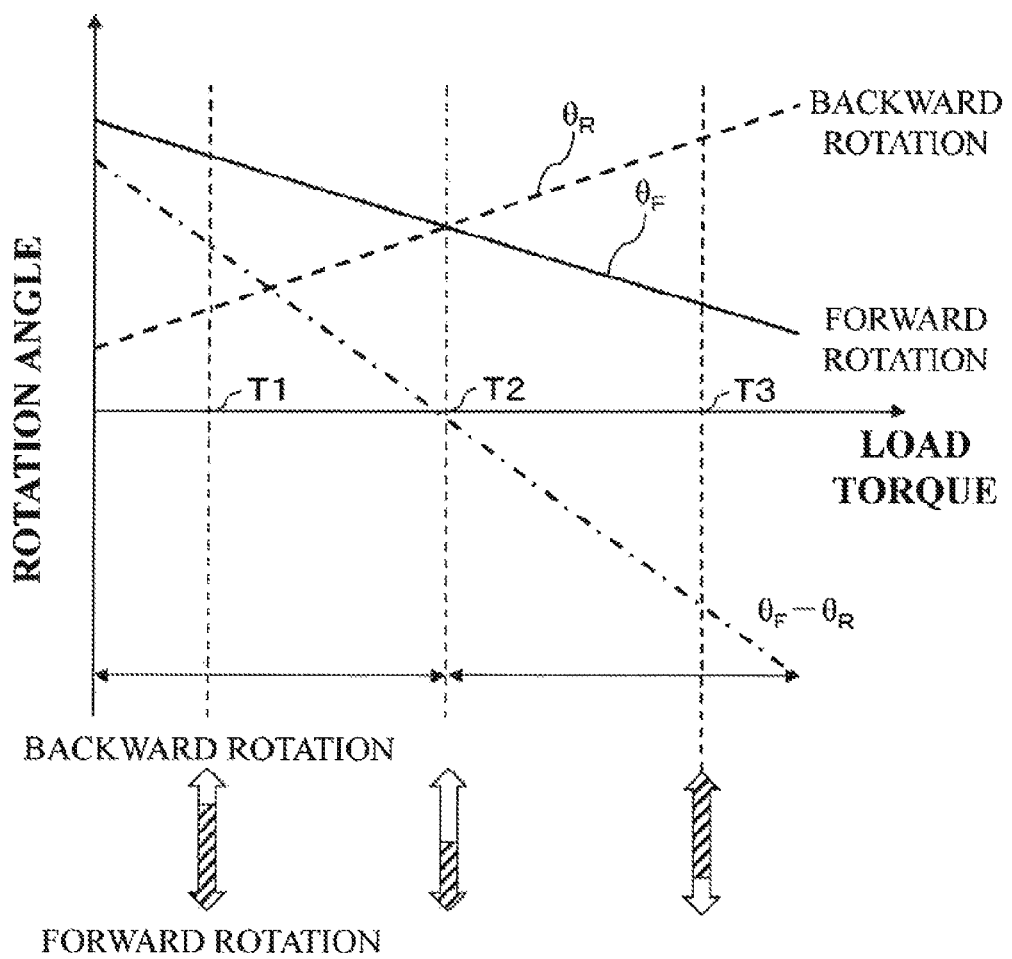
FIG. 3 is a graph illustrating a rotation angle for forward rotation and a rotation angle for backward rotation associated with a load torque.

In a graph shown in FIG. 3, the horizontal axis represents the load torque, and the vertical axis represents the rotation angle θ.

As shown in FIG. 3, the rotation angle $\theta_F$ for the forward rotation and the rotation angle $\theta_R$ for the backward rotation are set in a proportional relationship such that the rotation angle $\theta_F$ becomes smaller as the load torque becomes larger, and conversely, the rotation angle $\theta_R$ becomes larger as the load torque becomes larger. For example, at the time of a load torque T1, cutting is emphasized, so that the rotation angle $\theta_F$ (e.g., 150°) is set to be sufficiently larger than the rotation angle $\theta_R$ (e.g., 30°). At the time of a load torque T2 (>T1), balance between cutting and ejection of cut debris is emphasized, so that the rotation angle $\theta_F$ (e.g., 90°) and the rotation angle $\theta_R$ (e.g., 90°) are set to the same value. At the time of a load toque T3 (>T2), ejection of cut debris is emphasized, so that the rotation angle $\theta_R$ (e.g., 150°) is set to be larger than the rotation angle $\theta_F$ (e.g., 30°).

The control section 11 switches the relay 17 based on the set rotation angle $\theta_F$ and the set rotation angle $\theta_R$, to switch the polarity of the voltage applied to the motor 20 and forwardly and backwardly rotate the motor 20.

In the above example, while the load torque T1 is being measured, reciprocating rotation in which the motor is rotated forwardly through 150° and subsequently rotated backwardly through 30° is repeated. A net rotation angle of a file (a cutting tool) through one cycle including the forward rotation and the backward rotation is a difference between the rotation angle $\theta_F$ and the rotation angle $\theta_R$, i.e., $(\theta_F - \theta_R)$.

Next, after the load torque T2 is measured, reciprocating rotation in which the motor is rotated forwardly through 90°, and subsequently rotated backwardly through 90° is repeated.

Figure 4:
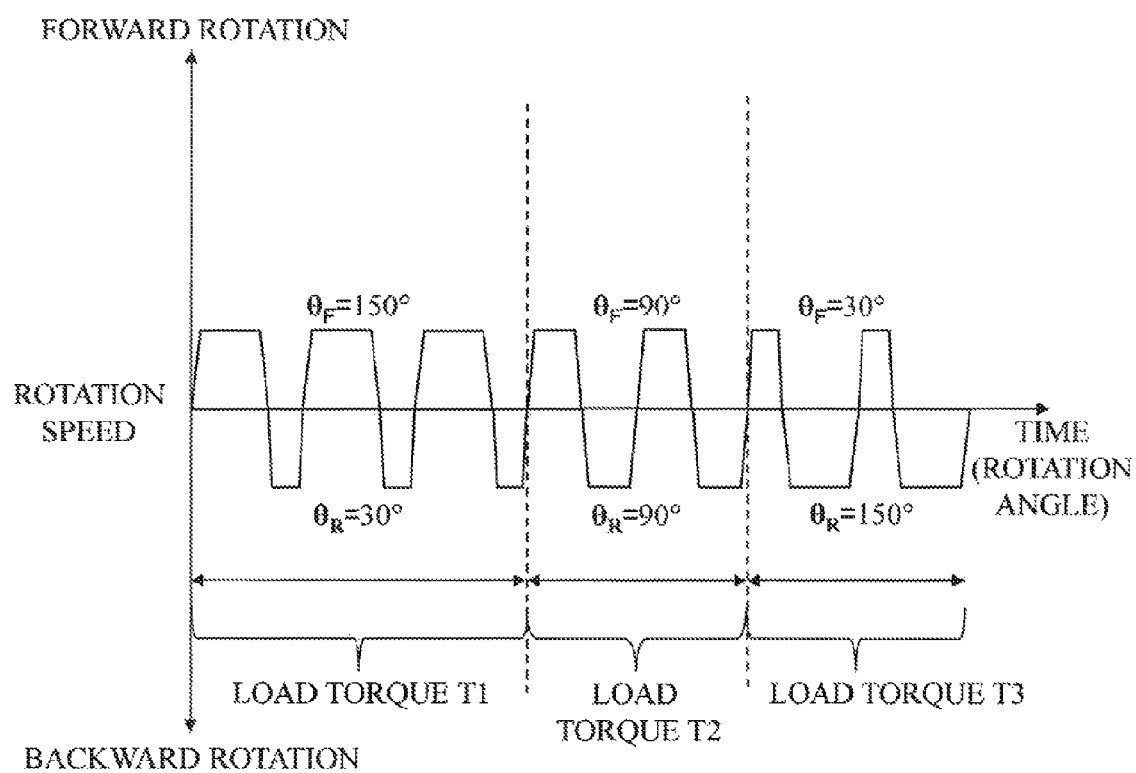
FIG. 4 is a graph illustrating one example of reciprocating rotation according to the first embodiment.

A state in which the motor 20 is rotated in the above example with the rotation angle $\theta_F$ (150°, 90°, 30°) and the rotation angle $\theta_R$ (30°, 90°, 150°) is shown in FIG. 4.

Accordingly, in the control apparatus 10 according to the present embodiment, the rotation angle $\theta_F$ for the forward rotation and the rotation angle $\theta_R$ for the backward rotation are determined according to the magnitude of the load torque, so that biting of the file can be reduced to prevent breakage thereof.

Second Embodiment

Although the example in which the load torque and the rotation angle $\theta_F$ and the rotation angle $\theta_R$ are in a proportional relationship is described in the first embodiment, the present invention is not limited thereto. The example is described in a second embodiment. In the second embodiment, the control apparatus 10 has a similar basic configuration to that of the first embodiment, and differences from the first embodiment are mainly described below.

Figure 5:
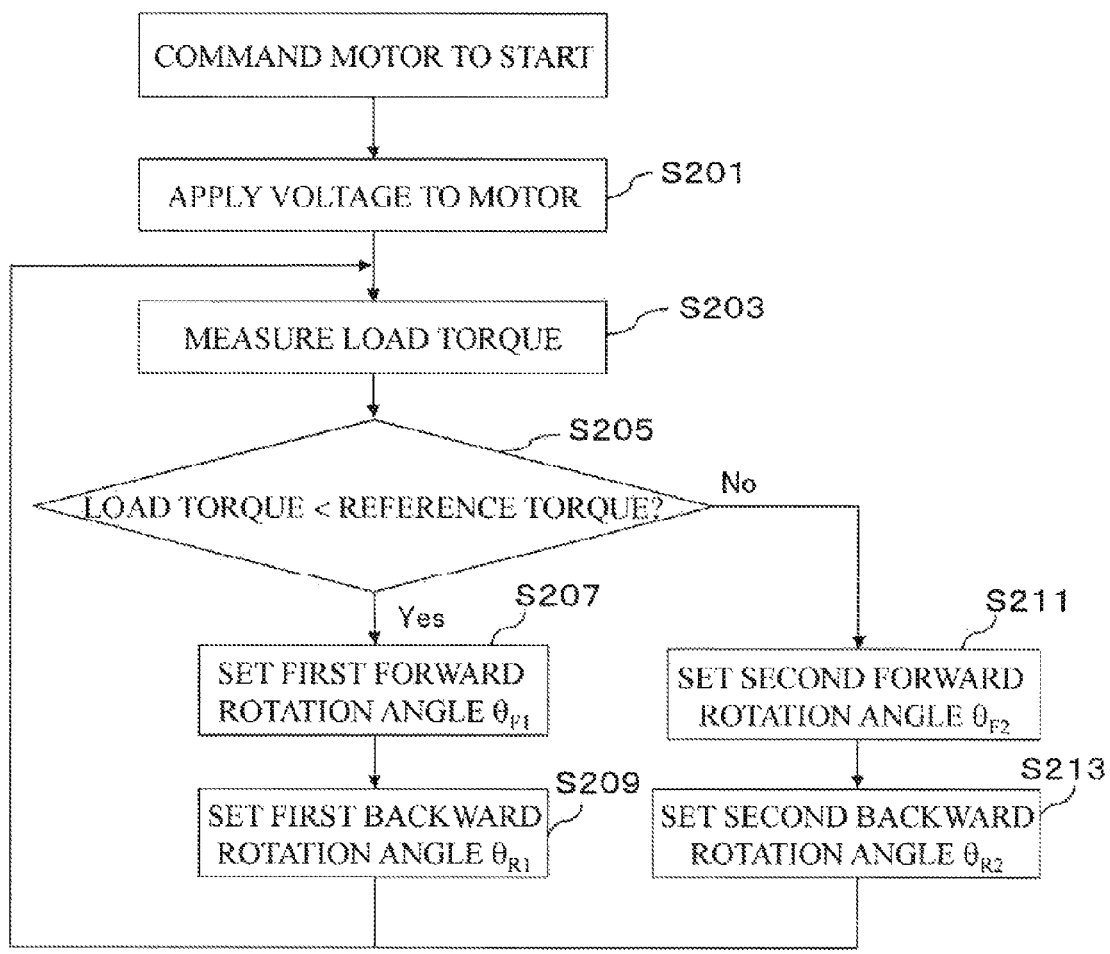
FIG. 5 is a view illustrating a control flow in a control apparatus according to a second embodiment.

The control apparatus 10 according to the second embodiment also measures the load torque as shown in FIG. 5 similarly to the first embodiment (step S201, S203). However, in the second embodiment, a reference torque is preliminarily set and retained in the setting section 13, and the control section 11 compares the measured load torque with the reference torque (step S205). When the load torque is less than the reference torque (Yes in step S205), a first forward rotation angle $\theta_{F1}$ and a first backward rotation angle $\theta_{R1}$ are set (step S207, S209). Meanwhile, when the load torque is equal to or more than the reference torque (No in step S205), a second forward rotation angle $\theta_{F2}$ and a second backward rotation angle $\theta_{R2}$ are set (step S211, S213).

Figure 6:
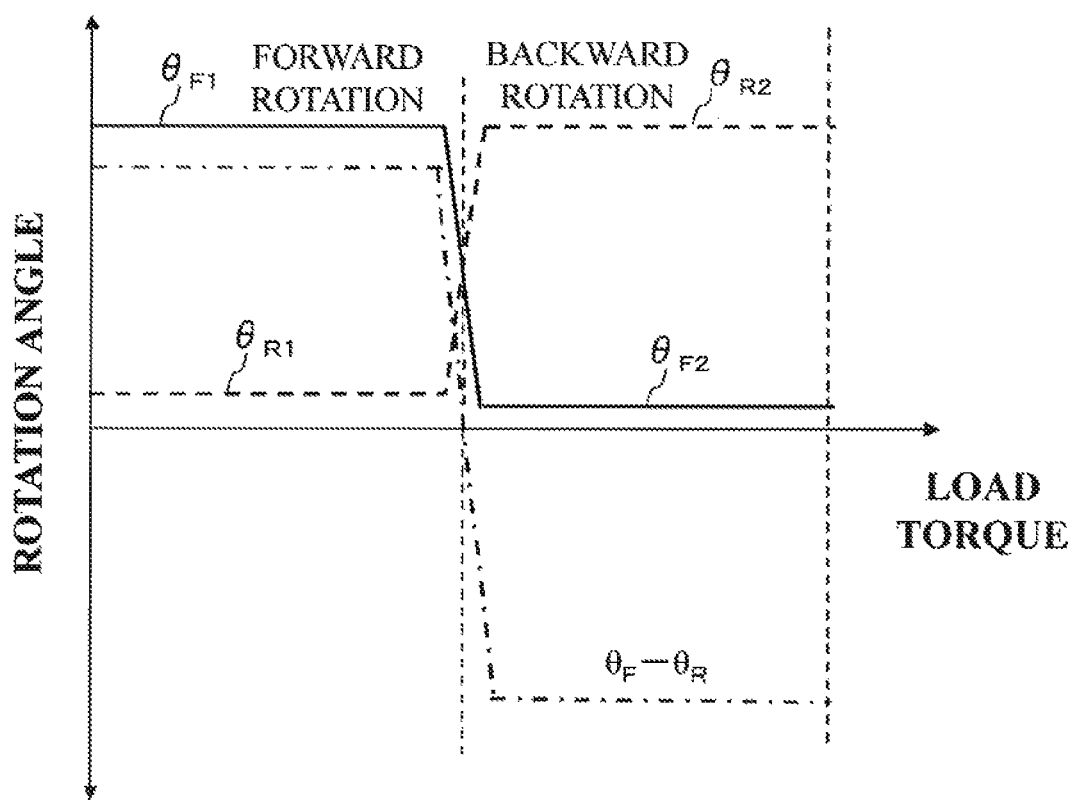
FIG. 6 is a graph illustrating a rotation angle for forward rotation and a rotation angle for backward rotation associated with a load torque.

One example of the first forward rotation angle $\theta_{F1}$, the first backward rotation angle $\theta_{R1}$, the second forward rotation angle $\theta_{F2}$, and the second backward rotation angle $\theta_{R2}$ is shown in FIG. 6.

As shown in FIG. 6, in the second embodiment, the second forward rotation angle $\theta_{F2}$ is set to be smaller than the first forward rotation angle $\theta_{F1}$, and the second backward rotation angle $\theta_{R2}$ is set to be larger than the first backward rotation angle $\theta_{R1}$ with a reference torque Tr as a boundary. That is, the second embodiment is similar to the first embodiment in that the forward rotation angle is increased when the load torque is small, and the backward rotation angle is increased when the load torque is large. The first forward rotation angle $\theta_{F1}$ to the second backward rotation angle $\theta_{R2}$ in FIG. 5 are merely one example of the present invention, and various aspects, for example, in one of which the first backward rotation angle $\theta_{R1}$ and the second backward rotation angle $\theta_{R2}$ are set to the same value may be employed.

As described above, the rotation angle $\theta_F$ for the forward rotation and the rotation angle $\theta_R$ for the backward rotation are also determined according to the magnitude of the load torque also in the second embodiment, so that biting of the file can be reduced to prevent breakage thereof. Particularly in the second embodiment, since the forward rotation angle is not reduced until the torque reaches the reference torque, it can be said that the second embodiment has a configuration in which cutting efficiency is more emphasized than in the first embodiment. On the other hand, it can be said that the example of the first embodiment has a configuration in which prevention of the breakage of the file is emphasized.

The control may be also executed by using both the information that the load torque and the rotation angle $\theta_F$ and the rotation angle $\theta_R$ are in a proportional relationship as in the first embodiment, and the information that the rotation angle $\theta_F$ and the rotation angle $\theta_R$ are identified based on the threshold value of the load torque as in the present embodiment.

Third Embodiment

Although the example in which the load torque is employed as the file state information is described in the above embodiments, the present invention is not limited thereto, and a root apex position may be employed as the file state information as described below in a third embodiment.

Figure 7:
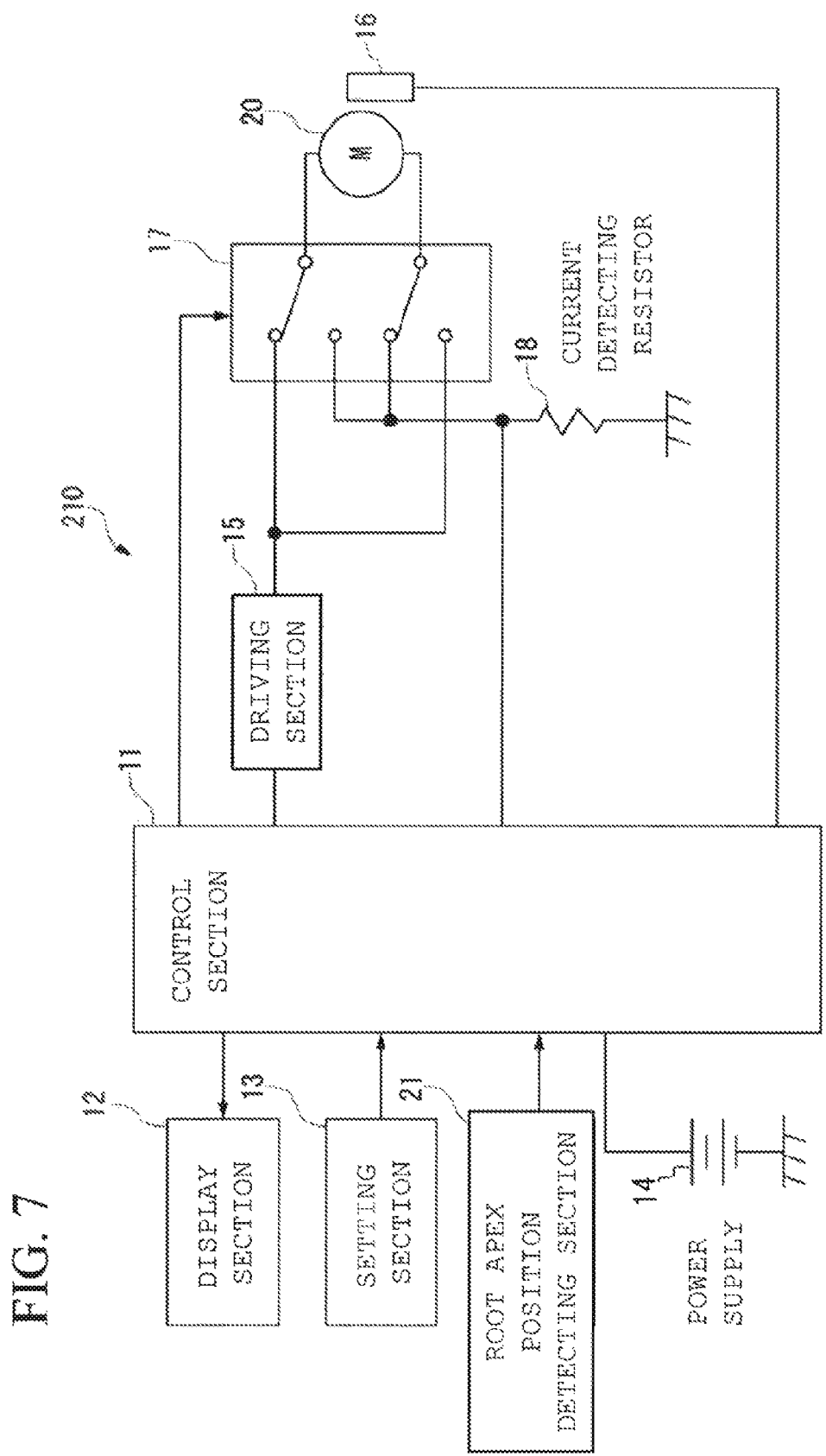
FIG. 7 is a view for explaining the configuration of a dental handpiece control apparatus in a third embodiment.

As shown in FIG. 7, a control apparatus 210 according to the third embodiment includes a root apex position detecting section 21, and the handpiece (not shown) in which the motor 20 is controlled by the control apparatus 210 includes a root apex length measuring function. The handpiece having the function measures a distance from a root apex to (the tip of) the file by detecting a root apex position while performing root canal treatment. That is, the root apex is detected by inserting the file, which is provided with a function as a measuring electrode, into the root canal of a tooth, and applying an electrical measurement signal between the file and an oral electrode that is separately provided. As a method for detecting a root apex by applying an electrical measurement signal between a measuring electrode and an oral electrode, at least a method of using a change in impedance within a root canal, a method of using a difference in impedance within a root canal, and a method of using an impedance ratio value within a root canal to detect a root apex are known, and any detection method including these methods may be employed in the present invention. The root apex position detecting section 21 provides a distance L between the measured root apex and the file to the control section 11.

The setting section 13 retains information regarding the rotation angle $\theta_F$ for the forward rotation and the rotation angle $\theta_R$ for the backward rotation corresponding to the distance L. The example is shown in FIG. 8, in which the horizontal axis in FIG. 3 is changed to the distance L.

Figure 8:
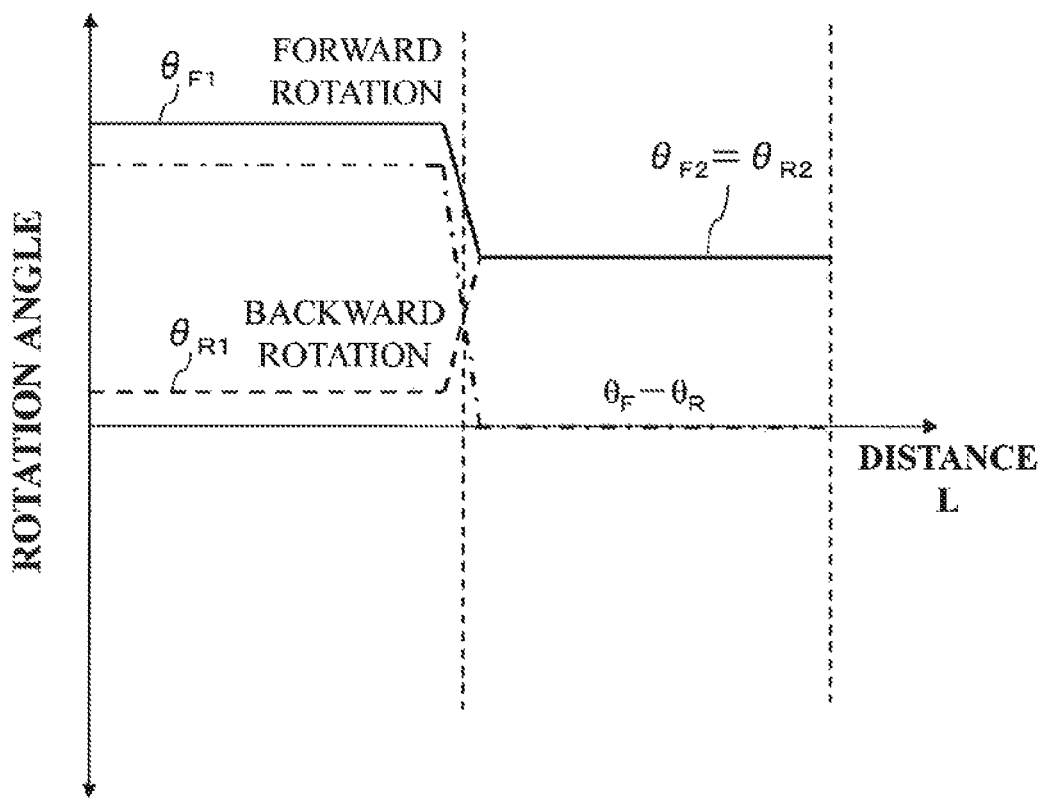
FIG. 8 is a graph illustrating a rotation angle for forward rotation and a rotation angle for backward rotation associated with a distance L.

The control section 11 acquires the rotation angles (the rotation angle $\theta_F$ and the rotation angle $\theta_R$ for the backward rotation) corresponding to the measured distance L, i.e., the information shown in FIG. 8 from the setting section 13, refers thereto, and controls the rotation of the motor 20 based on the rotation angles.

Normally, as the distance L between the root apex and the file is shorter, the file tends to bite; however, in accordance with the third embodiment, since the rotation angle $\theta_F$ for the forward rotation and the rotation angle $\theta_R$ for the backward rotation are determined according to the distance L, biting of the file can be reduced to prevent breakage thereof.

Although the embodiments of the present invention have been described above, the configurations described in the aforementioned embodiments may be also freely selected or changed into other configurations without departing from the scope of the present invention.

For example, although the examples in which the load torque and the distance L between the root apex and the file are used as the file state information are described, the rotation speed of the file (the motor) may be used as the file state information, or the present invention also allows the rotation angle $\theta_F$ for the forward rotation and the rotation angle $\theta_R$ for the backward rotation to be set based on an instruction from an operator in view of the feel of the file during treatment performed by the operator.

Also, although the presetting example in which the information that the file state information shown in FIGS. 3, 6, and 8 and the rotation angles are associated with each other is originally retained in the setting section 13 is described in the aforementioned embodiments, the information that the file state information and the rotation angles are associated with each other may be input to the setting section 13 by operator's manipulation, or the preset information may be also changed.

REFERENCE SIGNS LIST 10, 210 Control apparatus
11 Control section
12 Display section
13 Setting section
14 Power supply
15 Driving section
16 Sensor
17 Relay (rotation direction switching section)
18 Current detecting resistor
20 Motor
21 Root apex position detecting section

The invention claimed is:
1. A dental handpiece control apparatus for controlling a dental handpiece, the control apparatus comprising:

a rotation direction switching section that switches a polarity of a voltage applied to a motor, and thereby switches a rotation direction of the motor between a forward rotation angle and a backward rotation angle, the motor being incorporated in the dental handpiece to rotate a cutting tool mounted to the dental handpiece; and a control section that controls the switching of the voltage polarity by the rotation direction switching section based on the forward rotation angle and the backward rotation angle, wherein the forward rotation angle and the backward rotation angle are determined based on a load torque of the cutting tool, and the load torque of the motor and the forward rotation angle, and the load torque of the motor and the backward rotation angle, are respectively in a proportional relationship.

2. The dental handpiece control apparatus according to claim 1, wherein the rotation direction switching section is a relay.

3. The dental handpiece control apparatus according to claim 1, further comprising a root apex position detecting section that detects a distance between a root apex and a tip of the cutting tool, wherein the forward rotation angle and the backward rotation angle are further determined based on the distance.

4. The dental handpiece control apparatus according to claim 1, wherein as the load torque of the motor increases, the forward rotation angle decreases and the backward rotation angle increases.

5. The dental handpiece control apparatus according to claim 1, wherein:

when the load torque of the motor is a first predetermined value, the forward rotation angle is greater than the backward rotation angle;

when the load torque of the motor is a second predetermined value, the forward rotation angle is equal to the backward rotation angle;

when the load torque of the motor is a third predetermined value, the forward rotation angle is less than the backward rotation angle; and the first predetermined value is less than the second predetermined value and the second predetermined value is less than the third predetermined value.

6. The dental handpiece control apparatus according to claim 1, wherein:

when the load torque of the motor is a first predetermined value, the forward rotation angle is 150 degrees and the backward rotation angle is 30 degrees;

when the load torque of the motor is a second predetermined value, the forward rotation angle is 90 degrees and the backward rotation angle is 90 degrees;

when the load torque of the motor is a third predetermined value, the forward rotation angle is 30 degrees and the backward rotation angle is 150 degrees; and the first predetermined value is less than the second predetermined value and the second predetermined value is less than the third predetermined value.

7. The dental handpiece control apparatus according to claim 1, wherein the proportional relationship is a continuous linear relationship.

* * * * *